United States Patent [19]

Dubroeucq et al.

[11] 4,357,337
[45] Nov. 2, 1982

[54] INDENE DERIVATIVES, PROCESSES FOR THEIR PREPARATION, AND THEIR USE AS MEDICAMENTS

[75] Inventors: Marie-Christine Dubroeucq, Enghien-Les-Bains; Claude G. A. Guérémy, Houilles; Christian L. A. Renault, Taverny; Gérard R. Le Fur, Plessis Robinson, all of France

[73] Assignee: Pharmindustrie, Gennevilliers, France

[21] Appl. No.: 271,065

[22] Filed: Jun. 8, 1981

[30] Foreign Application Priority Data

Jun. 13, 1980 [FR] France .................................. 80 13145

[51] Int. Cl.³ .................. C07D 211/22; A61K 31/445
[52] U.S. Cl. .................................... 424/267; 546/205; 546/206
[58] Field of Search ................. 546/205, 206; 424/267

[56] References Cited

U.S. PATENT DOCUMENTS

| | | | |
|---|---|---|---|
| 3,340,268 | 9/1967 | Mizzoni | 546/205 |
| 3,476,759 | 11/1969 | Paragamian et al. | 546/205 |
| 3,644,372 | 2/1972 | Paragamian et al. | 546/206 |
| 3,984,407 | 10/1976 | Hauck et al. | 546/206 |
| 4,092,318 | 5/1978 | Hauck et al. | 546/206 |
| 4,172,945 | 10/1979 | Hauck et al. | 546/206 |

FOREIGN PATENT DOCUMENTS

| | | | |
|---|---|---|---|
| 881624 | 5/1980 | Belgium | 546/205 |
| 2269928 | 12/1975 | France | 546/206 |
| 1110087 | 4/1968 | United Kingdom | 546/206 |

*Primary Examiner*—Robert T. Bond
*Attorney, Agent, or Firm*—Beveridge, DeGrandi & Kline

[57] ABSTRACT

Compounds, which can be used as medicaments, of the formula:

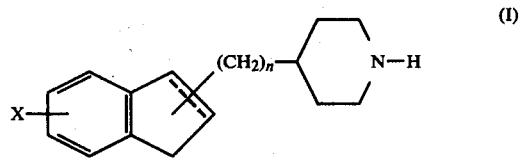

(I)

in which n is 1, 2 ore 3, X is fixed in position 4, 5, 6 or 7 on the cycle

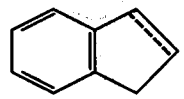

and represents a hydrogen atom or a halogen atom or an alkyl, alkoxy or alkylthio group having 1 to 4 carbon atoms, the

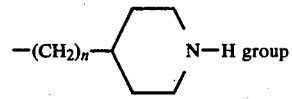 group is fixed in position 2 or 3 on the cycle

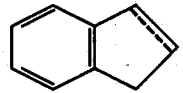

, and the broken line represents a second possible bond, are disclosed for the treatment of states of depression, as analgesics and anti-migraine substances.

15 Claims, No Drawings

INDENE DERIVATIVES, PROCESSES FOR THEIR PREPARATION, AND THEIR USE AS MEDICAMENTS

The present invention relates to new derivatives of indene which may be used as medicaments, notably as medicaments for the treatment of states of depression, as analgesics and anti-migraine substances.

These compounds can be represented by the general formula:

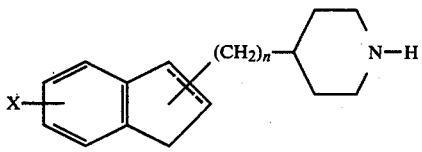

in which n is a whole number equal to 1, 2 or 3, X is fixed in in position 4, 5, 6 or 7 on the cycle

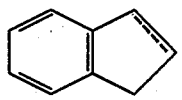

and represents a hydrogen atom, a halogen atom (especially chlorine or fluorine) or an alkyl, alkoxy, or alkylthio group having 1 to 4 carbon atoms, the

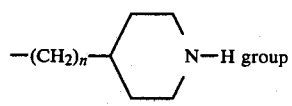

is fixed in position 2 or 3 on the cycle

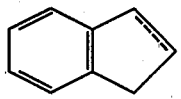

and the broken line represents a second possible bond.

As indicated by formula (I), the compounds according to the invention are derived either from indene, in which case they correspond to the formulae:

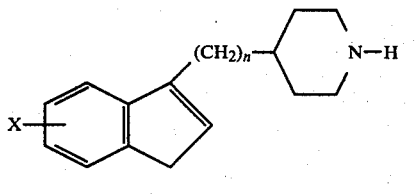

or

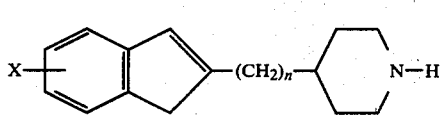

or from 2,3-dihydro 1H-indene or indane, in which case they correspond to the formula:

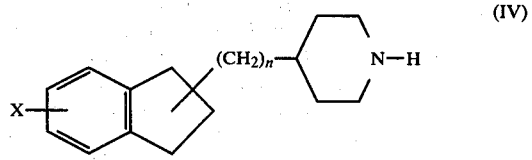

In formulae (I), (II), (III) and (IV), X is preferably a hydrogen atom.

The compounds of formula (II) can be prepared by reaction of an indene derivative of the formula:

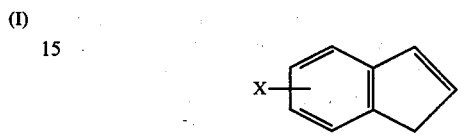

in which X has the same significance as in formula (I), with a metal derivative of formula RM, in which M indicates an alkali metal (in particular lithium, sodium or potassium) and R indicates a hydrogen atom, an $NH_2$ group, a mono-or di-substituted amino group in which the substituents are methyl, ethyl, isopropyl or cyclohexyl groups, an alkyl group containing from 1 to 5 carbon atoms or a phenyl group, reaction of the compound of formula (V) thus obtained with a piperidine derivative of the formula:

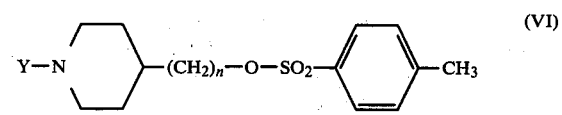

in which n is 1, 2 or 3 and Y represents a protecting group which can be removed in acid medium such as those described by R. A. Bolssonnas, Advances in Organic Chemistry, 3p150, Interscience (1963) in particular the triphenylmethyl group), and action of an acid on the compound of formula (VII) thus obtained. Suitable acids include inorganic acids such as hydrochloric acid, sulfuric acid, phosphonic acid, and organic acids such as formic acid, acetic acid, benzene- or paratoluenesulfonic acid and methanesulfonic acid. All the reactions can be shown diagrammatically as follows:

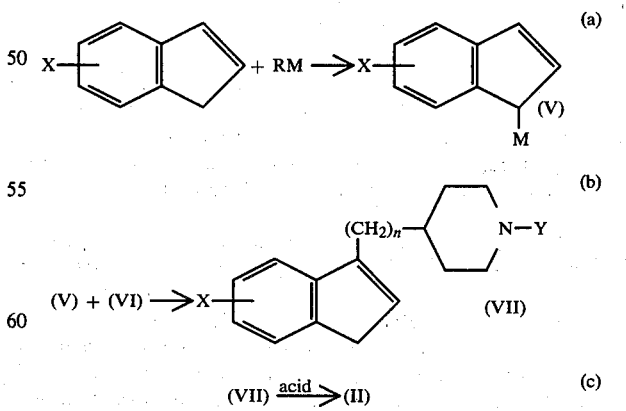

Reaction (a) is effected in an inert solvent, preferably an ether such as diethyl oxide, tetrahydrofuran or dimethoxyethane, at a temperature between 0° C. and the boiling temperature of the solvent used. As the metal derivative RM a lithium derivative is preferably used, for example phenyllithium, butyllithium or lithium diisopropylamide, in which case reaction (a) is effected at low temperature (0° C. to the ambient temperature).

The condensation reaction (b) is effected in the same solvents as reaction (a) and at a temperature between 0° C. and the boiling temperature of the solvent. When a lithium derivative is used as the metal derivative RM, reaction (b) is effected at a temperature between 0° C. and the ambient temperature.

Reaction (c), which consists in replacing the removable protecting group Y by a hydrogen atom, is effected according to methods known per se. For example, when Y is the triphenylmethyl group, reaction (c) may be effected by treating compound (VII) with a solution of an acid such as hydrochloric acid in a mixture of water and alcohol, at a temperature from 20° C. to 70° C. The alcohol may suitably be methanol, ethanol, propanol, isopropanol, or ethylene glycol, and the ratio of water to alcohol may be from 0.1:1 to 5:1.

The piperidine derivatives of formula (VI) for which Y is the triphenylmethyl group may be prepared by the action of triphenylmethyl chloride on esters of the formula:

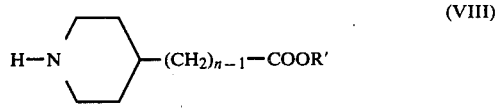

(VIII)

in which n is equal to 1, 2 or 3 and R' represents an alkyl group of low molecular weight, for example methyl or ethyl, reduction by lithium aluminum hydride LiAlH₄ of esters of the formula:

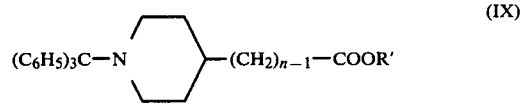

(IX)

thus obtained, and action of tosyl chloride on alcohols of the formula:

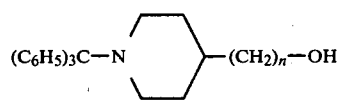

(X)

obtained.

The reaction of triphenylmethyl chloride with the esters of formula (VIII) is advantageously effected at a temperature of 20° C. to 25° C. in the presence of a base (preferably a tertiary amine such as triethylamine) and an inert solvent permitting solubilization of the reagents, for example chloroform.

Reduction of the esters of formula (IX) by LiAlH₄ is effected in an inert solvent, preferably an ether such as diethyl oxide or tetrahydrofuran, at a temperature between 0° C. and the ambient temperature.

The reaction of the tosyl chloride with the alcohols of formula (X) is effected at a temperature between 0° C. and the ambient temperature, in an inert solvent and in the presence of a base (preferably an amine). An advantageous method consists in operating in pyridine which plays both the role of solvent and of base.

The compounds of formula (III) can be prepared by dehydration in acid medium of the aminoalcohols of formula (XI) below, in which X and n have the same significance as in formula (I), Z represents a hydrogen atom or a group which can be removed in acid medium (for example the triphenylmethyl group) and the OH group is in position cis or in position trans with respect to

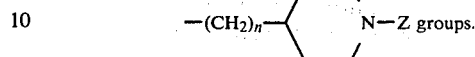

The reaction may be shown diagramatically as follows:

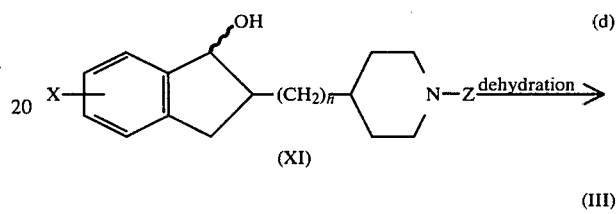

Reaction (d) is effected according to methods, known per se, which enable an alcohol to be dehydrated in acid medium and thus to be transformed into an olefin, for example those described by R. B. Wagner and H. D. Zook, Synthetic Organic Chemistry, p. 32, J. Wiley and Sons, 1965. An advantageous method consists in treating the aminoalcohols of formula (XI) with a 2 N to 6 N aqueous solution of sulfuric acid or with a solution of hydrochloric acid in a water-alcohol mixture, at a temperature of 40° C. to 80° C.

The aminoalcohols of formula (XI) can be prepared by reduction of ketones of the formula:

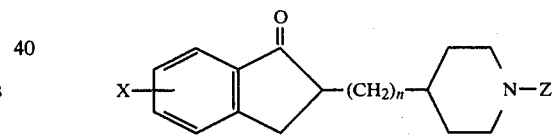

in which X and n have the same significance as in formula (I) and Z has the same significance as in formula (XI). In order to effect this reduction the reducing agent used is a hydride such as lithium aluminum hydride in an inert solvent, preferably an ether such as diethyl oxide or tetrahydrofuran. The reaction is effected at a temperature between 0° C. and the boiling temperature of the solvent.

The compounds of formula (IV) may be prepared by catalytic hydrogenation of the compounds of formulae (II) and (III) or their salts. This hydrogenation is effected in an inert solvent, at a temperature between 20° C. and 80° C. and under a hydrogen pressure of 1 to 50 bars. The solvent used may be, for example, alcohols, such as methanol or ethanol, or acids such as acetic acid. The hydrogenation catalyst used may be nickel, palladium, rhodium, ruthenium or platinum. When X represents a chlorine atom it is advantageous to use as solvent acetic acid, platinum as catalyst and to operate under a hydrogen pressure equal to atmospheric pressure.

The compounds of formula (IV) may also be prepared by catalytic hydrogenation, under conditions identical with those employed for the hydrogenation of compounds (II) and (III), of compounds of the formula:

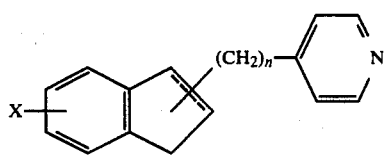

(XII)

in which X and n have the same significance as in formula (I), the

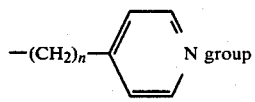

is fixed in position 2 or 3 on the cycle

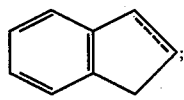

and the broken line represents a second possible bond.

The reaction mixtures obtained by the various processes previously described are treated according to conventional methods, physical (evaporation, extraction with a solvent, distillation, crystallization, chromatography, etc.) or chemical (formation of salt and regeneration of the base, etc.) in order to isolate the compounds of formula (I) in a pure state.

The compounds of formula (I) in the form of the free base may if desired by converted into salts of addition with a mineral or organic acid by the action of such an acid in a suitable solvent.

The following examples illustrate the invention without it being limited thereto. The data relating to the nuclear magnetic resonance spectra (in brief N.M.R.) appearing in the examples concern the nuclear magnetic resonance of the protons of the compounds in the form of a base in solution in deuterochloroform (unless the contrary is noted). The chemical shifts δ are measured by using tetramethylsilane as reference.

EXAMPLE 1

4-[3-(1H-indenyl)methyl]-piperidine (1) Preparation of ethyl [4-(1-triphenylmethyl)piperidine]carboxylate A solution of 50 g of ethyl (4-piperidine)carboxylate, 93.5 g of triphenylmethyl chloride and 97 ml of triethylamine in 500 ml of chloroform is stirred for 19 hours at the ambient temperature. The solvent is evaporated under reduced pressure, the residue is taken up with 600 ml of diethyl oxide, the insoluble material is filtered off and the filtrate is evaporated. An oily residue is obtained which is taken up with 600 ml of petroleum ether. The precipitate obtained is filtered and 80 g of ethyl [4-(1-triphenylmethyl)piperidine]carboxylate, which melts at 151° C., are thus obtained.

N.M.R. spectrum of the product obtained: protons of aromatic rings δ: 7 to 7.5 ppm; —O—$\underline{CH_2}$—CH$_3$ δ: 4.1 ppm; —O—CH$_2$—$\underline{CH_3}$ δ: 1.2 ppm.

(2) Preparation of [4-(1-triphenylmethyl)piperidine]-methanol

A solution of 10 g of ethyl [4-(1-triphenylmethyl)-piperidine] carboxylate in 120 ml of anhydrous tetrahydrofuran is added to a suspension of 1.9 g of lithium aluminum hydride in 40 ml of anhydrous tetrahydrofuran, placed in an atmosphere of nitrogen. After stirring for 3 hours at the ambient temperature, the reaction mixture is hydrolyzed by addition of 10 ml of water and 1 ml of a 5 N aqueous solution of sodium hydroxide. It is filtered and the filtrate is evaporated under reduced pressure. An oily residue is obtained which is taken up with petroleum ether. The precipitate obtained is filtered and 9.8 g of [4-(1-triphenylmethyl)piperidine]-methanol, which melts at 139° C., are thus obtained.

N.M.R. spectrum of the product obtained: protons of the aromatic rings δ: 7 to 7.5 ppm; —$\underline{CH_2}$—OH δ: 3.4 ppm.

(3) Preparation of 4-(p-tolylsulfonyloxymethyl)-1-triphenylmethyl-piperidine 9.6 g of p-methylphenylsulfonyl chloride are added, at 0° C., to 9.4 g of [4-(1-triphenylmethyl)piperidine]-methanol in 95 ml of pyridine. After 3 hours stirring at the ambient temperature, the reaction mixture is poured into 1 liter of water containing 75 ml of absolute ethanol. The mixture is stirred for 2 hours, the precipitate is filtered, washed with water and redissolved in chloroform. The organic phase is washed with water, dried over sodium sulfate and evaporated under reduced pressure. The oily residue obtained is taken up with petroleum ether. The precipitate obtained is filtered and 10 g of 4-[p-tolylsulfonyloxymethyl]-1-triphenylmethyl-piperidine, which melts at 192° C., are obtained.

N.M.R. spectrum of the product obtained:

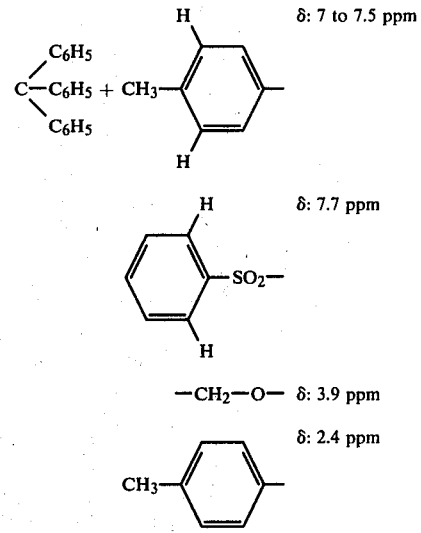

(4) Preparation of 4[3-(1H-indenyl)methyl]-piperidine 48 ml of a 2 M solution of butyllithium in hexane are added drop by drop, in 30 minutes, to a solution of 10.5 g of indene in 100 ml of tetrahydrofuran, cooled to 0° C. and placed under a nitrogen atmosphere. When the addition is complete, the reaction mixture is stirred for 2 hours at the ambient temperature, then cooled to 0° C.

Then a solution of 30.8 g of 1-triphenylmethyl-4-(p-tolylsulfonyloxymethyl)-piperidine in 180 ml of tetrahydrofuran is added in one hour. When the addition is complete, 50 ml of water are added, the tetrahydrofuran is evaporated under reduced pressure and the residue is extracted by 300 ml of diethyl ether. The ether phase is washed with water, dried over magnesium sulfate and concentrated.

The residue obtained (30 g) is dissolved in a mixture of 300 ml of ethanol and 150 ml of a 5 N aqueous solution of hydrochloric acid. The solution obtained is heated for 1½ hours at 45° C., then the ethanol is evaporated under reduced pressure. The residual aqueous phase is extracted 3 times with 200 ml of diethyl ether, then brought to pH 9 by addition of sodium hydroxide. The oil which salts out is extracted with ethyl acetate. The ethyl acetate phases are dried over magnesium sulfate and evaporated.

The oily residue obtained (9.5 g) is fixed on a column containing 300 g of silica, then eluted with a 90/10 chloroformdiethylamine mixture. 5.6 g of 4-[3-(1H-indenyl)methyl]-piperidine are thus obtained which, after treatment with a solution of hydrochloric acid in acetone, provide 6 g of 4-[3-(1H-indenyl)methyl]-piperidine hydrochloride. This latter product melts at 233° C.

EXAMPLE 2

4-{2-[3-(1H-indenyl)]ethyl}-piperidine (1) Preparation of methyl[4-(1-triphenylmethyl)piperidine]acetate The operation is as in the first part of Example 1, starting from 80 g of methyl(4-piperidine)acetate hydrochloride, 142 g of triphenylmethyl chloride and 200 ml of triethylamine in a liter of chloroform. 131 g of methyl [4-(1-triphenylmethyl)piperidine]acetate, which melts at 164° C., are obtained.

N.M.R. spectrum of the product obtained. protons of the aromatic rings δ: 7 to 7.5 ppm;

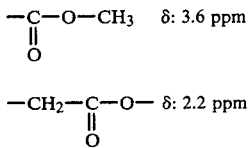

(2) Preparation of [4-(1-triphenylmethyl)piperidine]-ethanol

One operates as in the second part of the Example 1, starting from 3.5 g of lithium aluminum hydride and 18.4 g of methyl [4-(1-triphenylmethyl)piperidine] acetate in 300 ml of anhydrous tetrahydrofuran. 12.5 g of [4-(1-triphenylmethyl)piperidine]ethanol, which melts at 137° C., are obtained N.M.R. spectrum of the product obtained: protons of the aromatic rings δ: 7 to 7.5 ppm; —CH₂—OH δ: 3.5 ppm.

(3) Preparation of 4-[2-(p-tolylsulfonyloxy)ethyl]-1-triphenylmethyl-piperidine

The operation is effected as in the third part of Example 1, starting from 12 g of [4-(1-triphenylmethyl)-piperidine]-ethanol and 12.5 g of p-methylphenylsulfonyl chloride in 125 ml of pyridine. 17.5 g of 4-[2-(p-tolylsulfonyloxy)ethyl]-1-triphenylmethyl-piperidine, which melts at 176° C., are obtained.

N.M.R. spectrum of the product obtained:

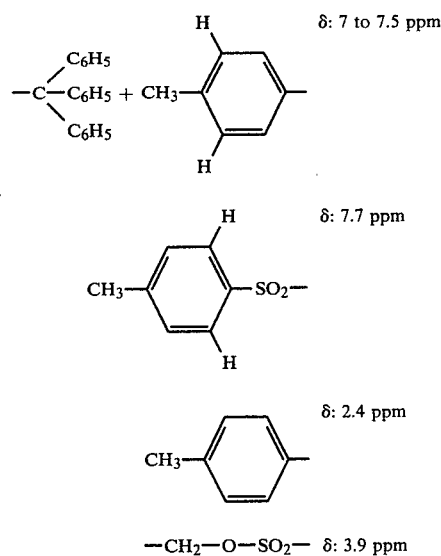

(4) Preparation of the 4-{2-[3-(1H-indenyl)]ethyl}-piperidine

One operates as in the fourth part of Example 1, using 9.85 g of indene, 45 ml of a 2 M solution of butyllithium in hexane and, instead of the 30.8 g of 1-triphenylmethyl-4-(p-tolylsulfonyloxymethyl)-piperidine, 29.8 g of 1-triphenylmethyl-4-[2-(p-tolylsulfonyloxy)ethyl]-piperidine. 3 g of 4-{2-[3-(1H-indenyl)]ethyl}-piperidine hydrochloride, which melts at 199° C., are obtained.

EXAMPLE 3

4-{3-[3-(1H-indenyl)]propyl}-piperidine (1) Preparation of ethyl 3-[4-(1-triphenylmethyl)piperidine]propionate One operates as in the first part of Example 1, starting from 57.7 g of ethyl 3-(4-piperidine)propionate, 86.9 g of triphenylmethyl chloride and 54 ml of triethylamine in 600 ml of chloroform. 125 g of ethyl 3-[4-(1-triphenylmethyl)piperidine]propionate are obtained, in the form of an oil.

N.M.R. spectrum of the product obtained: protons of the aromatic rings δ: 7 to 7.5 ppm; —CH₂—COOC₂H₅ δ: 2.3 ppm; —O—CH₂—CH₃ δ: 4.1 ppm.

(2) Preparation of 3-[4-(1-triphenylmethyl)piperidine]-propanol

One operates as in the second part of Example 1, starting from 1.9 g of lithium aluminum hydride and 12.6 g of ethyl 3-[4-(1-triphenylmethyl)piperidine]propionate in 150 ml of anhydrous tetrahydrofuran. 6.2 g of 3-[4-(1-triphenylmethyl)-piperidine]propanol, which melts at 124° C., are obtained.

N.M.R. spectrum of the product obtained: protons of the aromatic rings δ: 7 to 7.5 ppm; —CH₂—OH δ: 3.5 ppm.

(3) Preparation of 4-[3-(p-tolylsulfonyloxy)propyl]-1-triphenylmethyl-piperidine One operates as in the third part of Example 1, starting from 5.95 g of 3-[4-(1-triphenylmethyl)piperidine]-propanol and 5.9 g of p-methylphenylsulfonyl chloride in 60 ml of pyridine. 7.6 g of 4-[3-(p-tolylsulfonyloxy)-propyl]-1-triphenylmethylpiperidine, which melts at 131° C., are obtained.

N.M.R. spectrum of the product obtained:

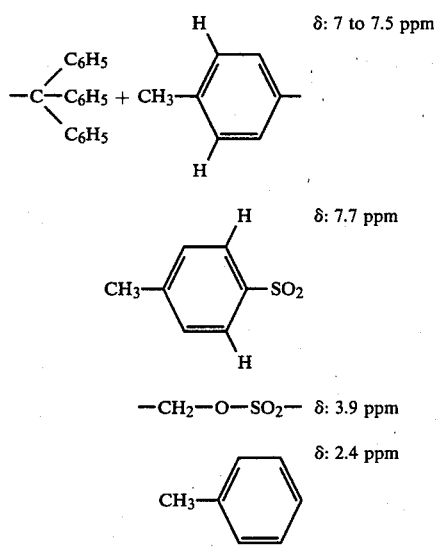

(4) Preparation of 4-{3-[3-(1H-indenyl)]propyl}piperidine

The operation is as in the fourth part of Example 1, using 11.3 g of indene, 52 ml of 2 M solution of butyllithium in hexane and, instead of the 30.8 g of 1-triphenyl-methyl-4-(p-tolylsulfonyloxymethyl)-piperidine, 35.1 g of 1-triphenylmethyl-4-[3-(p-tolylsulfonyloxy)propyl]-piperidine. 9 g of 4-{3-[3-(1H-indenyl)]propyl}piperidine hydrochloride, which melts at 170° C., are obtained.

EXAMPLE 4

4-[2-(1H-indenyl)methyl]-piperidine

(1) Preparation of 2-[(4-piperidinyl)methyl]-2,3-dihydro-1-1H-indenone (or 2-[(4-piperidinyl)methyl]-1-indanone).

60 g of 2-[(4-pyridyl)methyl]-2,3-dihydro-1-1H-indenone in solution in 600 ml of acetic acid are hydrogenated at the ambient temperature, under a pressure of 1 bar of hydrogen, in the presence of 3 g of platinum oxide Adams. After 7 hours of hydrogenation, the catalyst is eliminated by filtration and the filtrate is evaporated. The residue is fixed on a column containing 1600 g of silica and eluted with a 90/10 chloroform-diethylamine mixture. 30.2 g of a purified product, in the form of the free base, are thus obtained. This product is converted into the hydrochloride. After two recrystallizations of the said hydrochloride in ethanol, 13.3 g of the hydrochloride of 2[(4-piperidinyl)methyl]-2,3-dihydro-1-1H-indenone, which melts at 223° C., are obtained.

(2) Preparation of 2-[(4-piperidinyl)methyl]-2,3-dihydro-1-1H-indenol (or 2-[(4-piperidinyl)methyl]-1-indanol)

A solution of 2.4 g of 2-[(4-piperidinyl)methyl]-2,3-dihydro-1-1H-indenone in 24 ml of tetrahydrofuran is added in 15 minutes to a suspension of 0.38 g of lithium aluminum hydride in 24 ml of tetrahydrofuran, cooled to 0° C. and placed under an atmosphere of nitrogen. The mixture is stirred for 1 hour at 0° C., then 0.45 ml of water, 0.28 ml of a 5 N aqueous solution of sodium hydroxide and 1.25 ml of water are successively added. The mineral products are filtered off, and washed with methylene chloride. The filtrate and the washings are collected and evaporated. 2.3 g of 2-[(4-piperidinyl)methyl]-2,3-dihydro-1-1H-indenol are thus obtained in the form of a mixture of 75% of cis isomer and 25% of trans isomer.

N.M.R. spectrum of the product obtained:

The product obtained being represented by the global formula:

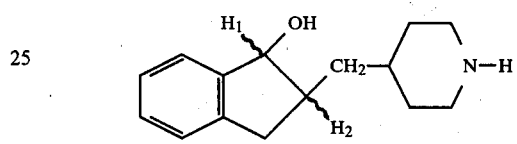

the spectral characteristics of the protons $H_1$ and $H_2$ fixed on the cycle are the following:
for the trans isomer:
$\underline{H}_1\delta=4.9$ ppm
$J_{H_1H_2}\to 5$ Hz
for the cis isomer:
$\underline{H}_1\delta=4.7$ ppm
$J_{H_1H_2}=7$ Hz

(3) Preparation of 4-[2-(1H-indenyl)methyl]-piperidine

A solution of 2.3 g of 2-[(4-piperidinyl)methyl]-2,3-dihydro-1-1H-indenol in 25 ml of a 4 N aqueous solution of sulfuric acid is heated at 60° C. for 2 hours. The solution, cooled to the ambient temperature, is brought to pH 10 by addition of sodium hydroxide. The oil which is salted out is extracted with ethyl acetate. The organic extract is washed with water, dried over magnesium sulfate and evaporated. The oily residue is fixed on a column containing 60 g of silica and is eluted with a mixture of 90 parts by volume of chloroform and 10 parts by volume of diethylamine (mixture 90/10 chloroform-diethylamine). 1.25 of 4-[2-(1H-indenyl)methyl]-piperidine in crystallized form are thus obtained, which is dissolved in 12 ml of acetone and treated with 0.85 ml of a 7 N solution of hydrochloric acid in diethyl ether. 1.35 g of 4-[2-(1H-indenyl)methyl]-piperidine hydrochloride, which melts at 234° C., are then obtained.

EXAMPLE 5

4-{3-2-(1H-indenyl)]propyl}-piperidine

(1) Preparation of 2-{3-[4-(1-triphenylmethyl)piperidinyl]propyl}-2,3-dihydro-1-1H-indenone.

21 g of sodium hydride (in the form of a 50% suspension in paraffin oil) are added portionwise to a solution of 29 g of 2,3-dihydro-1-1H-indenone in 240 ml of dimethoxyethane, placed in an atmosphere of nitrogen, then a solution of 27 g of 1-triphenylmethyl-4-(3-iodopropyl)-piperidine in 240 ml of dimethoxyethane is added, drop by drop, in a period of 45 minutes. After the addition, the mixture is stirred at the ambient temperature for 30 minutes, cooled in an ice bath and 100 ml of water, then 22 ml of acetic acid, then 800 ml of water are cautiously added. The mixture is extracted with diethyl ether, the ethereal extract is dried over magnesium sulfate and the diethyl ether is evaporated. The residue obtained (58 g) is fixed on a column containing 2000 g of silica and is eluted with a mixture of 90 parts by volume of cyclohexane and 10 parts by volume of ethyl acetate. 16.5 of 2-{3-[4-(1-triphenylmethyl)-piperidinyl]-propyl}-2,3-dihydro-1-1H-indenone are thus obtained.

N.M.R. spectrum of the product obtained:
The product obtained being represented by the formula:

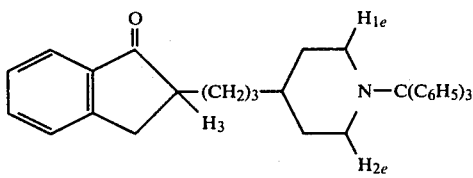

the spectral characteristics of the protons numbered $H_{1e}$, $H_{2e}$, $H_3$ are as follow:
$\underline{H}_{1e}$, $\underline{H}_{2e}$, $\underline{H}_3$ δ: 3 ppm (multiplet).

(2) Preparation of
2-{3-[4-(1-triphenylmethyl)piperidinyl]-propyl}-2,3-dihydro-1-1H-indenol.

The operation is as in the second part of Example 4, starting from 1.14 g of aluminum lithium hydride in 150 ml of tetrahydrofuran and 15 g of 2-{3-[4-(1-triphenyl-methyl)-piperidinyl]-propyl}-2,3-dihydro-1-1H-indenone in 150 ml of tetrahydrofuran. 14.8 g of 2-{3-[4-(1-triphenylmethyl)piperidinyl]-propyl}-2,3-dihydro-1-1H-indenol is thus obtained in the form of a mixture of 70% of cis isomer and 30% of trans isomer.

N.M.R. spectrum of the product obtained:
The product obtained being represented by the global formula:

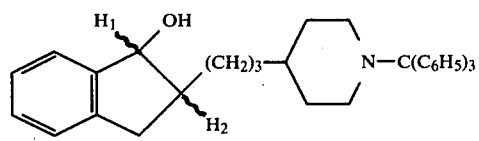

the spectral characteristics of the protons $H_1$ and $H_2$ fixed on the cycle are the following:
for the trans isomer:
$\underline{H}_1$ δ: 4.9 ppm;
$J_{H_1H_2} = 5$ Hz.
for the cis isomer:
$\underline{H}_1$ δ: 4.7 ppm;
$J_{H_1H_2} = 7$ Hz.

(3) Preparation of the
4-{3-[2-(1H-indenyl)]propyl}-piperidine 15 g of the 2-{3-[4-(1-triphenylmethyl)piperidinyl]-propyl}-2,3-dihydro-1-1H-indenol are dissolved in a mixture of 75 ml of 5 N aqueous solution of hydrochloric acid and of 150 ml of ethanol. The solution is maintained for 16 hours at the ambient temperature, then heated for 15 minutes at 45° C. The reaction mixture is diluted with 150 ml of water and the ethanol is evaporated under reduced pressure. The suspension obtained is brought to pH 3 by addition of sodium hydroxide and is extracted 3 times with 100 ml of diethyl ether each time, then brought to pH 10 by addition of sodium hydroxide. The oil which is salted out is extracted 3 times with 100 ml of ethyl acetate each time. The ethyl acetate extracts are washed with water, and dried over magnesium sulfate and evaporated. The residue obtained (6 g) is fixed on a column containing 120 g of silica and it is eluted with a 90/10 chloroform-diethylamine mixture. 5.1 g of the desired pure product are thus obtained, which is converted into the methanesulfonate by addition of a solution of methanesulfonic acid in acetone. 6 g of 4-{3-[2-(1H-indenyl)]-propyl}-piperidine methanesulfonate, which melts at 152° C., are then obtained.

EXAMPLE 6

4-{3-[1-(2,3-dihydro-1H-indenyl)]-propyl}-piperidine 3.6 g of 4-{3-[3-(1H-indenyl)]propyl}piperidine hydrochloride in solution in 40 ml of methanol are hydrogenated at the ambient temperature, under a hydrogen pressure of 1 bar, in the presence of 0.36 g of palladium in the form of palladium charcoal at 10% of palladium. After 1 hour the hydrogenation is ended. The catalyst is eliminated by filtration and the filtrate is evaporated to dryness. The crystalline residue is suspended in 70 ml of acetone. After draining and drying the crystals, 3.05 g of 4-{3[1-(2,3-dihydro-1H-indenyl)]propyl}-piperidine hydrochloride, which melts at 145° C., are obtained.

EXAMPLE 7

4-[2-(2,3-dihydro-1H-indenyl)methyl]-piperidine

The operation is as in Example 6 starting from 4 g of 4-[2-(1H-indenyl)methyl]-piperidine. 2.9 g of 4[2-(2,3-dihydro-1H-indenyl)methyl]-piperidine hydrochloride, which melts at 240° C., are obtained.

EXAMPLE 8

4-{3-[2-(2,3-dihydro-1H-indenyl)]propyl}-piperidine

The operation is as in Example 6 starting from 2.5 g of 4{3-[2-(1H-indenyl)]propyl}-piperidine. 2.2 g of 4-{3-[2-(2,3-dihydro-1H-indenyl)]propyl}-piperidine, of which the methanesulfonate melts at 134° C., are obtained.

EXAMPLE 9

4-[1-(2,3-dihydro-1H-indenyl)methyl]-piperidine (1) Preparation of 4-[3-(1H-indenyl)methyl]-pyridine A solution of 39.6 g of 2,3-dihydro-1-indenone in 80 ml of anhydrous tetrahydrofuran is reacted at 0° C. with a solution of lithium 4-methyl-pyridine, obtained by the action of 182 ml of a 2 N solution of butyllithium in hexane on 31 g of 4-methylpyridine dissolved in 300 ml of anhydrous tetrahydrofuran. Once the reaction has ended, 30 ml of water are added to the reaction mixture, then the tetrahydrofuran and hexane are eliminated by evaporation under reduced pressure. The residual aqueous suspension is brought to pH 1 by addition of a concentrated aqueous solution of hydrochloric acid. The precipitate obtained is filtered, washed with water, then with diethyl ether and with acetone, and dried. 25 g of 4-[3-(1H-indenyl)methyl]-pyridine, which melts at 210° C., are thus obtained.

(2) Preparation of
4-[1-(2,3-dihydro-1H-indenyl)methyl]-piperidine 35.5 g of 4-[3-(1H-indenyl)methyl]-pyridine hydrochloride in 400 ml of acetic acid are hydrogenated at atmospheric pressure and at the ambient temperature, in the presence of 3.5 g of platinum oxide Adams as catalyst. At the end of 8 hours, the catalyst is removed by filtration and the filtrate is evaporated under reduced pressure. The residue is taken up with 100 ml of water and the aqueous solution is brought to pH 11 by addition of sodium hydroxide. The oil which is salted out is extracted with chloroform. The organic phase is washed with water, dried and evaporated under reduced pressure. 31 g of the desired product are thus obtained in the form of an oil. This product is converted into the methanesulfonate by addition of a solution of methanesulfonic acid in acetone. After recrystallization of this salt in acetonitrile, 27 g of 4-[1-(2,3-dihydro-1H-indenyl)methyl]-piperidine methanesulfonate, which melts at 134° C., are obtained.

Analysis for $C_{15}H_{21}N$, $CH_3SO_3H$:

|  | % C | % H | % N |
|---|---|---|---|
| Calculated | 61.7 | 8.04 | 4.50 |
| Found | 61.5 | 8.10 | 4.30 |

EXAMPLE 10

4-[1-(5-methoxy-2,3-dihydro-1H-indenyl)methyl]-piperidine (1) Preparation of
4-[3-(6-methoxy-1H-indenyl)methyl]-pyridine One operates as in the first part of Example 9, but replacing the 2,3-dihydro-1-indenone by 5-methoxy-2,3-dihydro-1-indenone.

(2) Preparation of
4-[1-(5-methoxy-2,3-dihydro-1H-indenyl)-methyl]-piperidine 10.6 g of 4-[3-(6-methoxy-1H-indenyl)methyl]-pyridine dissolved in 100 ml of acetic acid are hydrogenated in the presence of 1 g of platinum oxide Adams, at atmospheric pressure and at a temperature of 30° C. After 5 hours the hydrogenation is finished. The catalyst is separated by filtration and the filtrate is evaporated. The residual oil is dissolved in 200 ml of water. The solution is brought to pH 5 by addition of an aqueous solution of sodium acid carbonate. The precipitate (traces of starting substance) is extracted with ethyl acetate. The aqueous solution is brought to pH 10 by addition of a 10 N solution of sodium hydroxide. The oil which is salted out is extracted by ethyl acetate. The organic phase is washed with water, dried over magnesium sulfate and evaporated. The residue (8.6 g) dissolved in acetone is treated with a 7 N solution of hydrochloric acid in diethyl ether (the solution of hydrochloric acid is added until the pH obtained is equal to 3). The crystals obtained are drained and dried. 9.1 g of 4-[1-(5-methoxy-2,3-dihydro-1H-indenyl)methyl]-piperidine hydrochloride, which melts at 226° C., are thus obtained.

EXAMPLE 11

4-[1-(6-chloro-2,3-dihydro-1H-indenyl)-methyl]-piperidine (1) Preparation of
4-[3-(5-chloro-1H-indenyl)methyl]-pyridine One operates as in the first part of Example 9, while replacing the 2,3-dihydro-1-indenone by 6-chloro-2,3-dihydro-1-indenone.

(2) Preparation of
4-[1-(6-chloro-2,3-dihydro-1H-indenyl)-methyl]-piperidine

One operates as in the second part of Example 10, while replacing at the start the 10.6 g of 4-[3-(6-methoxy-1H-indenyl)-methyl]-pyridine by 10.2 g of 4-[3-(5-chloro-1H-indenyl)-methyl]pyridine. 8.6 g of 4-[1-(6-chloro-2,3-dihydro-1H-indenyl)methyl]-piperidine hydrochloride, which melts at 222° C., are thus obtained.

EXAMPLE 12

4-[1-(6-methyl-2,3-dihydro-1H-indenyl)methyl]-piperidine (1) Preparation of
4-[3-(5-methyl-1H-indenyl)methyl]-pyridine One operates as in the first part of Example 9, while replacing the 2,3-dihydro-1-indenone by 6-methyl-2,3-dihydro-1-indenone.

(2) Preparation of
4-[1-(6-methyl-2,3-dihydro-1H-indenyl)-methyl]-piperidine

One operates as in the second part of Example 10, while replacing at the start the 10.6 g of 4-[3-(6-methyl-1H-indenyl)methyl]-pyridine by 6.8 g of 4-[3-(5-methyl-1H-indenyl)methyl]-pyridine hydrochloride. 4.2 g of 4-[1-(6-methyl-2,3-dihydro-1H-indenyl)methyl]-piperidine hydrochloride, which melts at 262° C., are thus obtained.

EXAMPLE 13

4-{2-[1-(2,3-dihydro-1H-indenyl)]-ethyl}-piperidine 20 g of 4-{2-[3-(1H-indenyl)]-ethyl}-pyridine in 200 ml of acetic acid are hydrogenated at atmospheric pressure and at the ambient temperature, in the presence of 2 g of platinum oxide Adams as catalyst. At the end of 3 hours the catalyst is removed by filtration and the filtrate is evaporated under reduced pressure. The residue is redissolved in 200 ml of water, the aqueous solution is brought to pH 10 by addition of sodium hydroxide and the oil which is salted out is extracted with chloroform. The organic phase is evaporated under reduced pressure. 21 g of the desired product are thus obtained in the form of an oil. This oil is converted into acid fumarate by the action of fumaric acid in ethanol. After a recrystallization in ethanol, 13.7 g of pure acid fumarate of 4-{2-[1-(2,3-dihydro-1H-indenyl)]-ethyl}-piperidine, which melts at 149° C., are obtained.

Elementary analysis for $C_{16}H_{23}N$, $C_4H_4O_4$:

|  | % C | % H | % N |
|---|---|---|---|
| Calculated | 69.57 | 7.83 | 4.06 |
| Found | 69.6 | 7.9 | 4.1 |

The 4-{2-[3-(1H-indenyl)]ethyl}-pyridine can be prepared as indicated in U.S. Pat. No. 3,300,506.

EXAMPLE 14

4-{2-(2-(2,3-dihydro-1H-indenyl)]-ethyl}-piperidine (1) Preparation of 1-[2-(2,3-dihydro-1H-indenyl)]-2-(4-pyridyl-1-ethanone.

To a solution, cooled to −72° C. and placed under a nitrogen atmosphere, of 1.9 g of ethyl [2-(2,3-dihydro-1H-indenyl)]carboxylate in 10 ml of anhydrous tetrahydrofuran, is added drop by drop, in 1 hour 30 minutes, a solution of lithium 4-methyl-pyridine obtained by the action of 10 ml of a 2 N solution of butyllithium in hexane on 1.95 ml of 4-methyl-pyridine dissolved in 20 ml of anhydrous tetrahydrofuran. When the addition is ended, 5 ml of ethanol are added and the reaction mixture is allowed to return to the ambient temperature. The solvents are evaporated and 50 ml of an N aqueous solution of hydrochloric acid are added to the residue. The insoluble material is extracted with diethyl ether and the residual aqueous phase is brought to pH 7 by addition of an aqueous solution of sodium acid carbonate. The oil which is salted out is extracted by ethyl acetate. The organic extract is dried over magnesium sulfate and evaporated. 2 g of 1-[2-(2,3-dihydro-1H-indenyl)]-2-(4-pyridyl)-1-ethanone are thus obtained.

(2) Preparation of 4-{2-[2-(2,3-dihydro-1H-indenyl)]-ethyl}-pyridine

The 2 g of 1-[2-(2,3-dihydro-1H-indenyl)]-2-(4-pyridyl)-1-ethanone obtained in the preceding stage are heated at 120° C. for 10 minutes with 1.52 ml of 85% hydrazine hydrate and 6.5 ml of diethyleneglycol. 1.5 g of potassium hydroxide are added and the reaction mixture is heated at 160° C. for 1 hour. It is allowed to return to the ambient temperature, 60 ml of water are added, and the insoluble material is extracted with diethyl ether. The ethereal extract is dried over magnesium sulfate and evaporated. The oily residue (1.6 g) is fixed on a column of silica and eluted with ethyl acetate. 1.2 g of 4-{2-[2-(2,3-dihydro-1H-indenyl)]ethyl}-pyridine, which melts at 59° C., are thus obtained.

(3) Preparation of 4-{2-[2-(2,3-dihydro-1H-indenyl)]-ethyl}-piperidine 1.2 g of 4-{2-[2-(2,3-dihydro-1H-indenyl)]-ethyl}-pyridine dissolved in 12 ml of acetic acid are hydrogenated in the presence of 0.12 g of platinum oxide Adams, at the atmospheric pressure and at ambient temperature. After 6 hours the hydrogenation is ended. The catalyst is separated by filtration and the filtrate evaporated. 50 ml of water are added to the residual oil and the insoluble material is extracted with diethyl ether. The aqueous solution is brought to pH 9 by addition of a 10 N aqueous solution of sodium hydroxide. The oil which is salted out is extracted with diethyl ether. The ethereal extract is washed with water, dried over magnesium sulfate and evaporated. The residue (1.1 g) is dissolved in ethanol and is treated with a 6 N solution of hydrochloric acid in diethyl ether (the hydrochloric acid solution is added until the pH is equal to 2). The crystals obtained are drained and dried. 0.95 g of 4-{2-[2-(2,3-dihydro-1H-indenyl)]-ethyl}-piperidine hydrochloride, which melts at 198° C., are thus obtained.

PHARMACOLOGICAL PROPERTIES

Antidepressive activities

The activity of the products of formula (I) has been demonstrated by means of the inhibition test of the uptake of serotonine by synaptosomes of the rat brain (cortex), according to the method of Kannengiesser et Coll. (Biochem. Pharmacol. 22, 73, 1973). The results are expressed by a 50% inhibiting dose ($I_{50}$) which represents the dose of product, in micromoles per liter, decreasing by 50% the uptake of the serotonine.

The results obtained are collected in the following table:

TABLE

| Products | $I_{50}$ (μM/l) |
|---|---|
| Example 2 | 0.009 |
| Example 3 | 0.05 |
| Example 7 | 0.4 |
| Example 9 | 0.4 |
| Example 10 | 0.2 |
| Example 11 | 0.3 |
| Example 12 | 0.25 |
| Example 13 | 0.004 |
| Example 14 | 0.005 |

The compounds of formula (I) are therefore powerful inhibitors of the uptake of serotonine.

Toxicological Properties

The acute toxicities of the compounds of formula (I) have been determined on the male mouse $CD_1$ (Charles River) by oral administration. The $DL_{50}$ have been calculated, after 3 days observation, by the cumulative method of J. J. Reed and H. Muench (Amer. J. Hyg., 27, 493, 1938).

The compounds of formula (I) behave like substances of relatively little toxicity towards mice, since the $DL_{50}$ of the compounds are between 200 and 1000 mg/kg.

Therapeutic Utilization

The compounds according to the invention and their pharmaceutically acceptable salts may be used in human therapeutics, in the form of compressed tablets, capsules, gelatin-coated pills, suppositories, injestable or injectable solutions, etc., for the treatment of the pathological states engendered by a disturbance of the functioning of the serotoninergical systems, especially as anti-depressants, as regulators of the serotonine-dependent vascular tonicity (especially for the treatment of migraines) and as analgesics.

The posology depends on the effects sought and the method of administration used. For example, taken orally, it may comprise between 15 and 250 mg of active substance per day, with single doses ranging from 5 to 50 mg.

What is claimed is:
1. A compound of the formula:

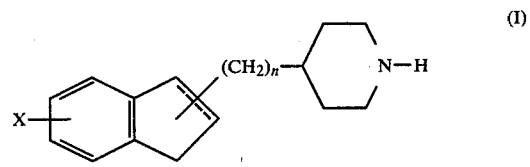

in which n is a whole number equal to 1, 2 or 3, X is fixed in position 4, 5, 6 or 7 on the cycle

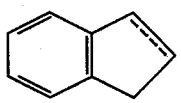

and represents a hydrogen atom, a halogen atom or an alkyl, alkoxy or alkylthio group having 1 to 4 carbon atoms, the

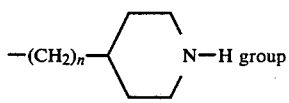

is fixed in position 2 or 3 on the cycle

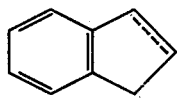

and the broken line represents a possible second bond, and its salt of addition with an acid selected from the group consisting of hydrochloric acid, sulfuric acid, phosphoric acid, formic acid, acetic acid, benzenesulfonic acid, paratoluenesulfonic acid, methanesulfonic acid and fumaric acid.

2. A compound according to claim 1, having the formula:

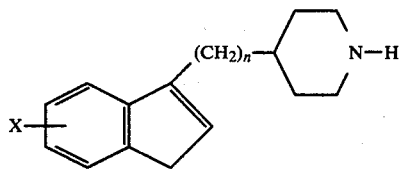

in which X and n have the same significance as in claim 1, and its salt of addition with an acid selected from the group consisting of hydrochloric acid, sulfuric acid, phosphoric acid, formic acid, acetic acid, benzenesulfonic acid, paratoluenesulfonic acid, methanesulfonic acid and fumaric acid.

3. A compound according to claim 1 of the formula:

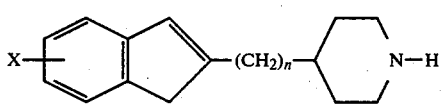

in which X and n have the same significance as in claim 1, and its salt of addition with an acid selected from the group consisting of hydrochloric acid, sulfuric acid, phosphoric acid, formic acid, acetic acid, benzenesulfonic acid, paratoluenesulfonic acid, methanesulfonic acid and fumaric acid.

4. A compound according to claim 1 of the formula:

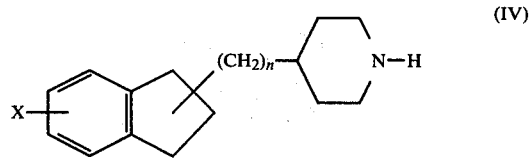

in which X and n have the same significance as in claim 1, and its salt of addition with an acid selected from the group consisting of hydrochloric acid, sulfuric acid, phosphoric acid, formic acid, acetic acid, benzenesulfonic acid, paratoluenesulfonic acid, methanesulfonic acid and fumaric acid.

5. A compound according to claim 1, 2, 3 or 4 in which X is a hydrogen atom and its salt of addition with an acid selected from the group consisting of hydrochloric acid, sulfuric acid, phosphoric acid, formic acid, acetic acid, benzenesulfonic acid, paratoluenesulfonic acid, methanesulfonic acid and fumaric acid.

6. Compound according to claim 2 of the formula:

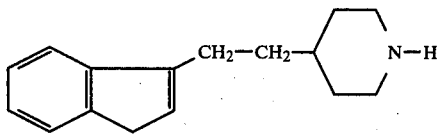

and its salt of addition with an acid selected from the group consisting of hydrochloric acid, sulfuric acid, phosphoric acid, formic acid, acetic acid, benzenesulfonic acid, paratoluenesulfonic acid, methanesulfonic acid and fumaric acid.

7. Compound according to claim 4 of the formula:

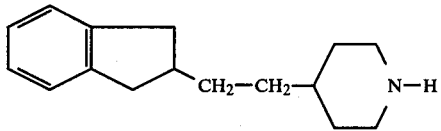

and its salt of addition with an acid selected from the group consisting of hydrochloric acid, sulfuric acid, phosphoric acid, formic acid, acetic acid, benzenesulfonic acid, paratoluenesulfonic acid, methanesulfonic acid and fumaric acid.

8. Process for the preparation of a compound according to claim 2, in which a compound of the formula:

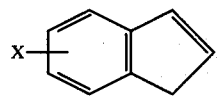

in which X has the same significance as in claim 2, is reacted with a metal derivative having the formula RM, in which M is an alkali metal and R is a hydrogen atom, an $NH_2$ group, a mono-substituted or disubstituted amino group in which the substituents are methyl, ethyl, isopropyl or cyclohexyl groups, an alkyl group having 1 to 5 carbon atoms or a phenyl group, the compound of the formula:

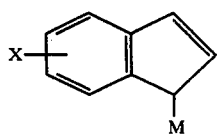 (V)

thus obtained is reacted with a piperidine derivative of the formula:

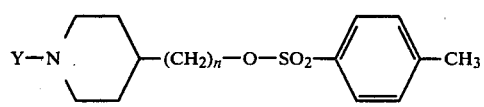 (VI)

in which n is 1, 2 or 3 and Y is a protecting group which can be removed in acid medium, and the compound of formula:

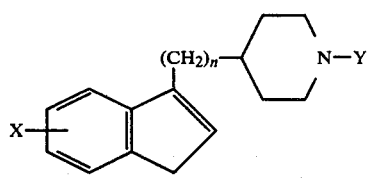 (VII)

thus obtained is subjected to the action of an acid.

9. Process for the preparation of a compound according to claim 3, in which an aminoalcohol of the formula:

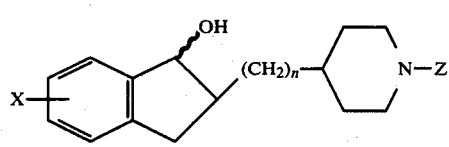 (XI)

in which X and n have the same significance as in claim 3 and Z represents a hydrogen atom or a group which can be removed in acid medium, is dehydrated in acid medium.

10. Process for the preparation of a compound according to claim 4, in which a compound according to claim 2 or claim 3 or a salt thereof is subjected to a catalytic hydrogenation.

11. Process for the preparation of a compound according to claim 4, in which compounds of the formula:

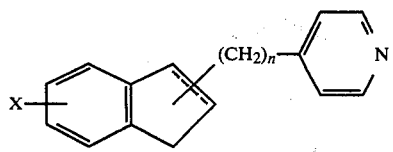 (XII)

in which X and n have the same significance as in claim 4, the broken line indicates a possible second bond and the

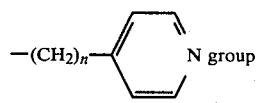 group is fixed in position 2 or 3 on the cycle

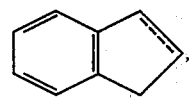, is subjected to a catalytic hydrogenation.

12. Medicament, particularly useful as an antidepressive, antimigraine and analgesic, which contains a pharmaceutically acceptable carrier and, as active principle, 5 to 50 mg per unit dose of a compound corresponding to formula (I) of claim 1 or a salt of said compound with a pharmaceutically acceptable acid.

13. Medicament according to claim 12 which contains, as active principle, 5 to 50 mg per unit dose of the compound of the formula:

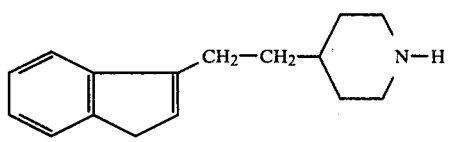

or a salt of this compound with a pharmaceutically acceptable acid.

14. Medicament according to claim 12 which contains, as active principle, 5 to 50 mg per unit dose of the compound of the formula

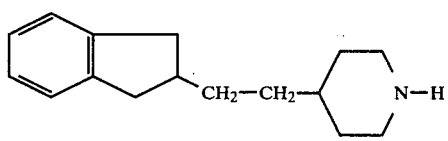

or a salt of this compound with a pharmaceutically acceptable acid.

15. A process for treating a human suffering from depression, migraine or pain which comprises orally administering to said human 15 to 250 mg per day of a compound corresponding to formula (I) of claim 1 or a salt thereof with a pharmaceutically acceptable acid.

* * * * *